(12) United States Patent
Liao

(10) Patent No.: US 10,208,029 B2
(45) Date of Patent: *Feb. 19, 2019

(54) PHOTOACID COMPOSITIONS HAVING EXTENDED LIFETIME OF PROTON DISSOCIATION STATE

(71) Applicant: University of Central Florida Research Foundation, Inc., Orlando, FL (US)

(72) Inventor: Yi Liao, Melbourne, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/057,856

(22) Filed: Mar. 1, 2016

(65) Prior Publication Data

US 2016/0251343 A1    Sep. 1, 2016

Related U.S. Application Data

(63) Continuation-in-part of application No. 13/748,253, filed on Jan. 23, 2013, now Pat. No. 9,708,257.

(51) Int. Cl.
| | |
|---|---|
| *C07D 417/06* | (2006.01) |
| *C07D 209/12* | (2006.01) |
| *C07D 403/06* | (2006.01) |
| *C07D 307/68* | (2006.01) |
| *C07D 405/08* | (2006.01) |

(52) U.S. Cl.
CPC ......... *C07D 417/06* (2013.01); *C07D 209/12* (2013.01); *C07D 307/68* (2013.01); *C07D 403/06* (2013.01); *C07D 405/08* (2013.01)

(58) Field of Classification Search
None
See application file for complete search history.

(56) References Cited

U.S. PATENT DOCUMENTS

2013/0192978 A1 *   8/2013   Liao ..................... C07D 209/12
                                                               204/157.71

OTHER PUBLICATIONS

Shi, et al., JACS, 133:14699 (Aug. 8, 2011).*
Villemin, et al., Synthetic Communications, 31:1771 (2001).*

* cited by examiner

*Primary Examiner* — Michael Barker
(74) *Attorney, Agent, or Firm* — Stephen C. Thomas; Jon M. Gibbs

(57) ABSTRACT

A photoacid includes a nucleophilic (NuH) moiety having a photodissociable proton, an electron accepting (EA) moiety, and a bridge structure (X) bonded to both the NuH moiety and EA moiety positioned between the NuH and EA moieties. The NuH and EA moieties each include respective structure so that the EA moiety bonds to a proton photodissociated form of the NuH moiety during a reversible photoinduced intramolecular reaction to form a ring, which has been found to significantly increase the lifetime of the proton dissociation state.

20 Claims, 8 Drawing Sheets

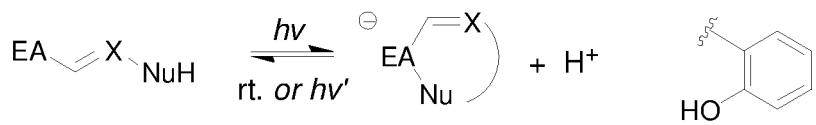 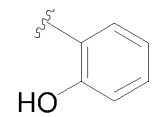
FIG 3A            FIG 3B
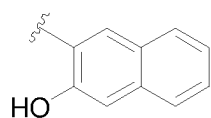 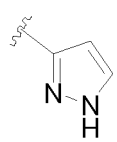 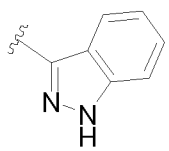
FIG 3C      FIG 3D      FIG 3E
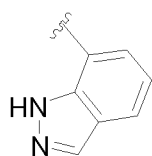 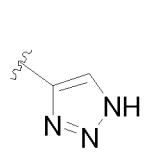 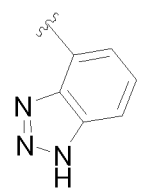
FIG 3F      FIG 3G      FIG 3H
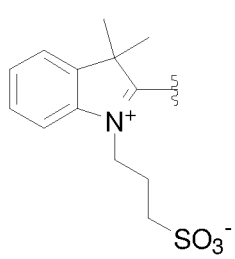 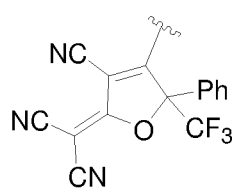 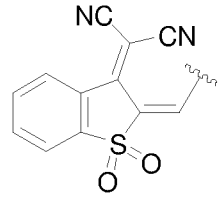
FIG 3I      FIG 3J      FIG 3K
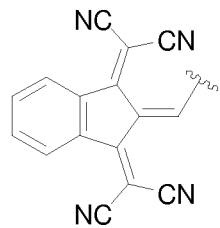 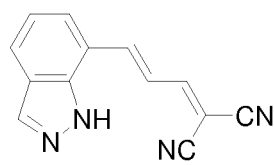
FIG 3L      FIG 3M

PHOTOACID COMPOSITIONS HAVING EXTENDED LIFETIME OF PROTON DISSOCIATION STATE

CROSS REFERENCE TO RELATED APPLICATIONS

This application claims the benefit U.S. patent application Ser. No. 13/748,253, entitled "PHOTOACID HAVING EXTENDED LIFETIME OF PROTON DISSOCIATION STATE", filed Jan. 23, 2013, currently pending, which claims the benefit of Provisional Application Ser. No. 61/592,232 entitled "PHOTOACID HAVING EXTENDED LIFETIME OF PROTON DISSOCIATION STATE", filed Jan. 30, 2012, which are incorporated herein by reference in their entirety.

U.S. GOVERNMENT RIGHTS

Disclosed embodiments were made with U.S. Government support under Contract Number 1239759 with the National Science Foundation (NSF) and Contract Number FA9550-09-1-0628 with the Air Force Office of Scientific Research (AFOSR). The U.S. Government thus has certain rights to this invention.

FIELD

Disclosed embodiments relate to photoacids and methods of using photoacids.

BACKGROUND

Proton transfer is one of the most fundamental processes in nature. Proton transfer is involved in numerous chemical reactions, biological functions and material properties. Photoacids are molecules that undergo proton ($H^+$) dissociation upon irradiation, and may be defined as any compound convertible into a strong acid by photolysis. Photoacids promise spatial and temporal control of these processes in a noncontact way, and can also provide a way to convert photoenergy into other types of energy (e.g., electrical energy). As used herein, the term "photoacid" refers to the molecules that reversibly undergo proton photodissociation and thermal reassociation, under photo-irradiation and in the dark, respectively. The reassociation may also be induced by photo-irradiation at a wavelength different from the wavelength that induces proton dissociation.

Photoacids have been studied for several decades, and several reviews on photoacids have been published. Photoacids have been used to study molecular proton transfer, and have been exploited to control molecular and supramolecular events. However, the photo-induced proton concentration of reported photoacids has not been sufficient to drive or control many acid catalyzed or pH-sensitive processes, so that the potential of photoacids has yet to be realized. For example, catalyzing reactions using photoacids was first proposed in the 1970s and is still described as a potential application in some recent published papers.

A major challenge using photoacids for processes involving proton transfer is that the lifetime of the proton-dissociation state is limited by the lifetime of the conjugated base of the photoacid in the ground state. The short lifetime of the proton dissociation state is useful for studying some fast processes. However, the liberated proton does not have enough time to diffuse away from its counter ion and thus cannot catalyze a chemical process or significantly alter a macroscopic property even though the theoretical excited-state acid dissociation constant ($pKa^*$) can be very low. One recent work reported a photoacid with a relaxation time of the proton dissociation state close to 1 second, which was estimated by pump-probe absorption spectroscopy.

SUMMARY

Disclosed embodiments include long-lived photoacid compositions compared to known photoacid compositions that have structures which undergo a reversible photo-induced intramolecular reaction after proton dissociation that stabilizes the proton dissociation state to significantly increase the lifetime of the proton dissociation state. Using disclosed photoacids, acid-catalyzed and pH-sensitive processes can be controlled or driven by visible or ultraviolet (UV) light irradiation. Disclosed photoacids can also be applied to a variety of other applications, including, but not limited to, materials, biomedicine, energy conversion and other processes involving proton transfer.

Disclosed photoacids generally include a nucleophilic moiety (NuH), an electron accepting moiety (EA), and a bridge structure (X) providing a connection between the NuH and EA. The NuH and EA are selected to have respective structures so that the EA bonds during a photo-induced intramolecular reaction to the proton dissociated form of the NuH after proton dissociation of the NuH to form a ring, which has been found to significantly increase the lifetime of the proton dissociation state.

BRIEF DESCRIPTION OF THE DRAWINGS

FIG. 2B shows the photoreaction of an example PAH according to an example embodiment shown as photoacid 1 that has a structure which combines a phenolic moiety as the NuH and a indoline moiety as the EA. The sulfonic moiety ($R-SO_2O^-$) functions as the counter ion of the liberated proton, while

FIG. 3A shows a generalized disclosed PAH structure and its nucleophilic ring closing reaction to yield the generalized product including an extra ring shown and a proton.

FIGS. 3B-H show several example NuH structures, according to example embodiments.

FIGS. 3I-L show several example EA structures, according to example embodiments.

FIG. 3M shows an example of a disclosed PAH that does not have a ring in the EA moiety, according to an example embodiment.

DETAILED DESCRIPTION

Figure 1A:
FIG. 1A shows a mechanism for a known photoacid.

Disclosed embodiments in this Disclosure are described with reference to the attached figures, wherein like reference numerals are used throughout the figures to designate similar or equivalent elements. The figures are not drawn to scale and they are provided merely to illustrate the disclosed embodiments. Several aspects are described below with reference to example applications for illustration. It should be understood that numerous specific details, relationships, and methods are set forth to provide a full understanding of the disclosed embodiments. One having ordinary skill in the relevant art, however, will readily recognize that the subject matter disclosed herein can be practiced without one or more of the specific details or with other methods. In other instances, well-known structures or operations are not shown in detail to avoid obscuring structures or operations that are not well-known. This Disclosure is not limited by the illustrated ordering of acts or events, as some acts may occur in different orders and/or concurrently with other acts or events. Furthermore, not all illustrated acts or events are required to implement a methodology in accordance with this Disclosure.

Notwithstanding that the numerical ranges and parameters setting forth the broad scope of this Disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5.

Figure 1B:
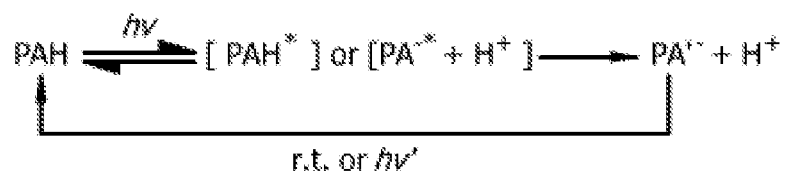
FIGS. 1B and 1C show example mechanisms for disclosed photoacids according to an example embodiment, where "PAH" stands in these FIGs and herein for photoacid.
Figure 1C:
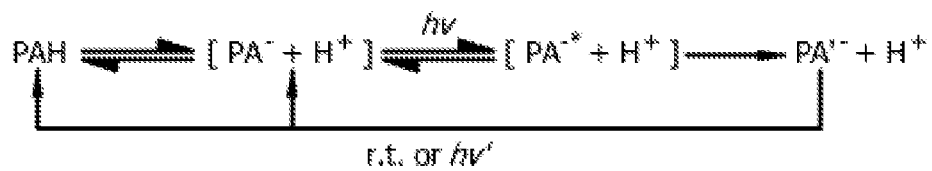

FIG. 1A shows a mechanism of a known PAH, and FIG. 1B and FIG. 1C first and second example proposed mechanisms for disclosed PAHs, respectively. Any mechanism described herein is believed to explain the observations and measurements made. However, although the mechanisms described herein are believed to be accurate, disclosed embodiments may be practiced independent of the particular mechanism(s) that may be operable.

As illustrated in FIG. 1A the mechanism for the known PAH is a single step where the PAH photodissociates to form an excited photoacid anion $PA^{-*}$ and a proton $H^+$. The photoinduced proton dissociation state has a short lifetime, such as <1 second.

In contrast, disclosed PAHs have structures that enable the excited photoacid PAH* (mechanism 1 shown in FIG. 1B) or its anionic part $PA^{-*}$ (mechanism 2 shown in FIG. 1C) formed from photodissociation of PAH to undergo a second reaction comprising a reversible photoinduced intramolecular photoreaction which forms a ring, that results in formation of $PA'^{-}+H^+$, which can be either an adiabatic or non-adiabatic process. Since the proton dissociation form provided ($PA'^{-}+H^+$) is at a ground state, it can be very stable. In addition, the acidity of the proton dissociation state depends on the basicity of the anion $PA'^{-}$.

Figure 2A:
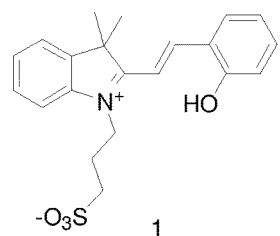
FIG. 2A shows an example embodiment of photoacid 1.
Figure 2B:
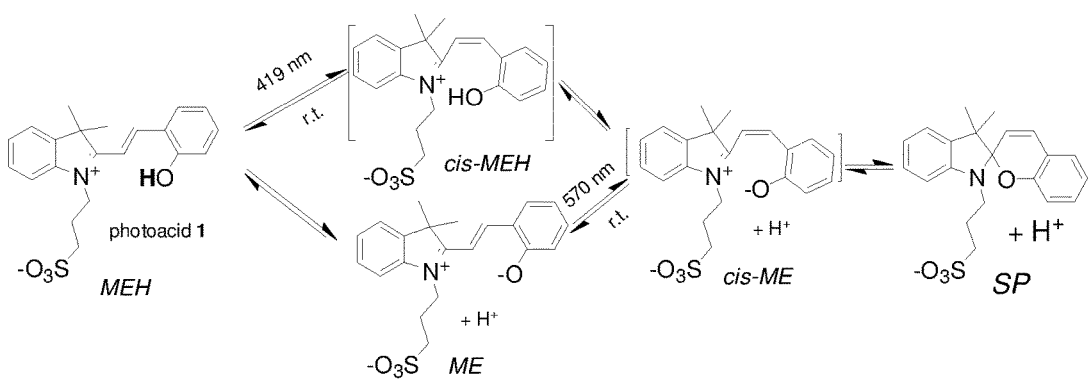

Photoacid 1 shown in FIG. 2B as MEH comprises an example disclosed PAH comprising a protonated photochromic merocyanine (MEH) with a propyl sulfonate group on the nitrogen of the indoline moiety. It was discovered that photoacid 1 can reversibly change the proton concentration of its solution by over 100 times.

Figure 2C:
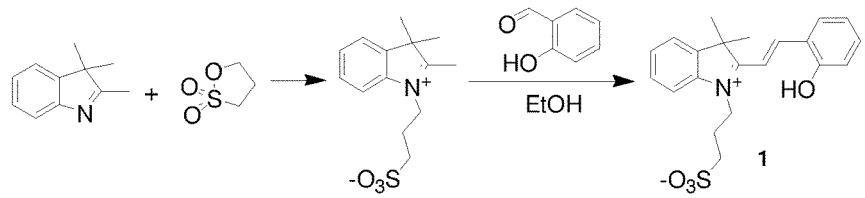
FIG. 2C shows one example synthesis route for forming photoacid 1.

MEH can be synthesized following the example procedure shown in FIG. 2C. In an aqueous solution, the MEH form of 1 is predominantly at room temperature in the dark, which was proven by UV-Vis and NMR spectroscopy. In the UV-Vis spectrum, the absorption of the deprotonated merocyanine (ME) can also be observed, which indicates that photoacid 1 is weakly acidic. A $5.88 \times 10^{-4}$ M aqueous solution of photoacid 1 has a pH value of 5.5 at 25° C., from which the pKa of photoacid 1 was calculated to be 7.8.

When the solution was irradiated with a 419 nm light, which is close to the $\lambda_{max}$ of MEH (424 nm), the photoreaction of the MEH resulted in a pH drop by more than 2 units to 3.3. This value is close to the theoretical value for complete proton dissociation (pH=3.2) indicating that photoacid 1 is a strong acid under irradiation at a wavelength near $\lambda_{max}$. Proton dissociation of the cis-MEH produces cis-ME, which undergoes a nucleophilic ring closing reaction to yield the product shown as SP in FIG. 2B and a proton. The product formed by the ring closing process has a stabilized proton dissociation state.

When the light was turned off, the pH value increased quickly to ~4.5 in ~1 min, gradually returning to its original level in ~5 min. This cycle can be repeated many times. Therefore, the proton concentration in a solution having photoacid 1 can be simply controlled by switching a visible light source on and off. Significantly, this process does not require control of two different light sources with different wavelengths, nor does it involve irradiation with UV light.

The mechanism shown in FIG. 2B is a general mechanism and disclosed PAHs are not limited to the merocyanine (MEH) or tricyanofuran (TCF) type PAHs as disclosed below. For example, the phenolic moiety may be substituted by other structures that have a weakly acidic proton. Heteroaromatic structures with more than one nitrogen atoms can also be used. Such heteroaromatic structures can include indazole, pyrazole, benzotriazole, and triazole. The N—H acidity of these structures is often lower than the acidity of phenol ($pK_a$=9.95), which results a low dark acidity. In the ring-closed (proton dissociation) form, the corresponding heterocyclic structures have very low basicity, and thus do not significantly lower the photo-induced acidity. For example, the $pK_a$ (N—H) of indazole is 13.86 and the $pK_a$ of its conjugated acid is 1.25, which means that a $pK_a$ change of 12.61 may be achieved upon photoirradiation.

FIG. 3A shows a generalized disclosed PAH structure and its nucleophilic ring closing reaction to yield the generalized product including an extra ring shown and a proton. The PAH is shown as an EA moiety bound to a NuH moiety by a bridge structure "X" which is bonded to both the NuH and EA and is thus positioned between the NuH and EA moieties. In the presence of light close to the $\lambda_{max}$ of the PAH, the EA moiety bonds to a proton photodissociated form of the NuH moiety during a reversible photoinduced intramolecular reaction to form the ring shown including EA, Nu and X.

The EA moiety and NuH moiety for disclosed PAHs may be embodied by a variety of different EA and NuH moieties. FIGS. 3B-H show several example NuH moiety structures with (d)-(h) being heteroaromatic structures with more than one nitrogen atom.

FIGS. 3I-M show several example EA moiety structures. Although the EA and NuH structure shown in FIGS. 3B-M all have at least one ring, a ringed structure is not required.

For example, FIG. 3M shows an example of a disclosed PAH that does not have a ring in the EA moiety.

Regarding bridge structures (X), X can comprise CH or N which can bond to a C from the EA moiety to form a C=C or C=N bond (bridge) to the EA moiety, respectively. It is known that spirooxazines with a C=N bridge have better reversibility and fatigue resistance than spiropyrans with a C=C bridge. Therefore, using N as a bridge structure to provide a C=N bridge for disclosed PAHs may also improve reversibility and fatigue resistance. These new types of PAHs can not only to enhance photo-induced acidity, but can also control the absorption wavelength, increase the quantum yields of the photoreactions, and improve the reversibility.

Figure 4:
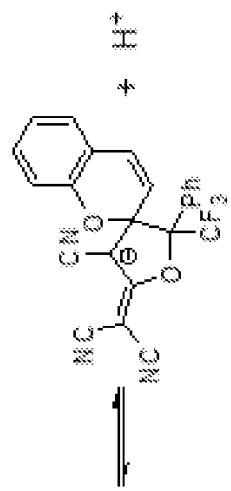
FIG. 4 shows structures for example tricyanofuran (TCF) photochromic compounds and their photoreaction, according to an example embodiments.
Figure 4:
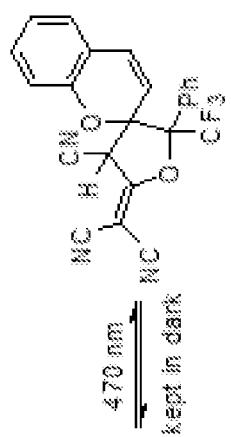
Figure 4:
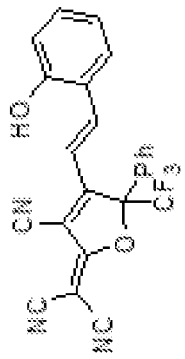

Given the positive results obtained from merocyanine type photoacids such as photoacid 1 described above, tricyanofuran (TCF) type molecules were considered useful as PAHs, with an example TCF-based PAHs shown in FIG. 4 and its photoreaction including a PAH in FIG. 4 shown as photoacid 40 having a $CF_3$-tricyanofuran (CF3-TCF) acceptor. Photoacid 1 and the TCF photochromic compound shown in FIG. 4 are actually structurally similar to each other since they all have a phenolic moiety that provides the active proton and determines the acidity before irradiation. The phenolic moiety is linked to an EA moiety with a double bond. Upon irradiation, the two moieties undergo a nucleophilic reaction after the proton dissociation of the phenol and a trans-cis isomerization, which generates a cyclic structure.

The TCF compound shown in FIG. 4 showed negative photochromism, high quantum yields and good reversibility. Photoacid 40 shown in FIG. 4 is a particularly effective PAH since the proton on CF3-TCF in the photo-induced form is expected to be very acidic. In one study, the pH value of a solution of photoacid 40 in ethanol changed from 5.44 to 2.21 upon irradiation at 470 nm. Compared to photoacid 1, photoacid 40 has better compatibility with organic solvents and materials, and thus may be more suitable for some applications.

Figure 6A:
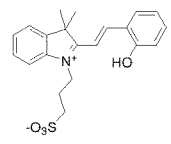
FIGS. 6A-QQ show example PAH structures for synthesized PAH compounds according to example embodiments.
Figure 6B:
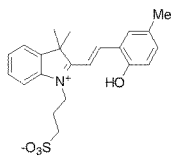
Figure 6C:
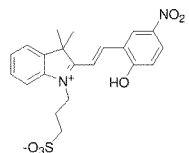
Figure 6D:
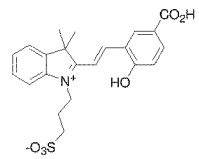
Figure 6E:
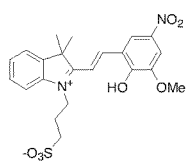
Figure 6F:
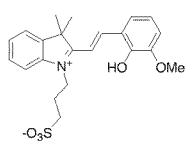
Figure 6G:
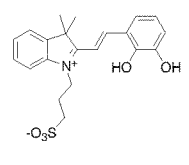
Figure 6H:
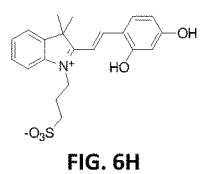
Figure 6I:
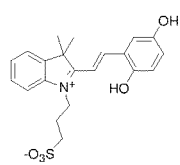
Figure 6J:
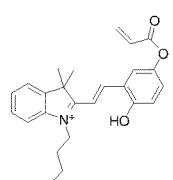
Figure 6K:
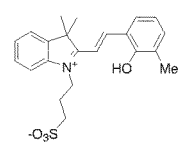
Figure 6L:
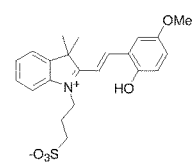
Figure 6M:
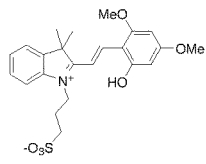
Figure 6N:
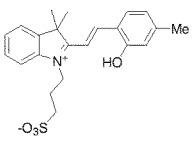
Figure 6O:
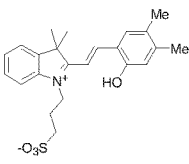
Figure 6P:
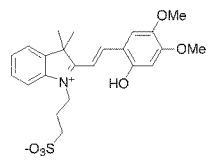
Figure 6Q:
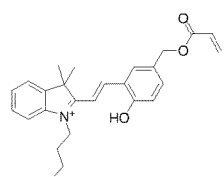
Figure 6R:
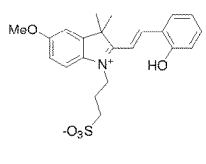
Figure 6S:
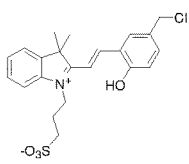
Figure 6T:
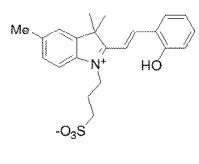
Figure 6U:
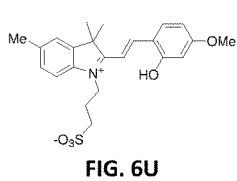
Figure 6V:
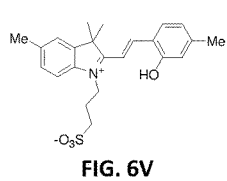
Figure 6W:
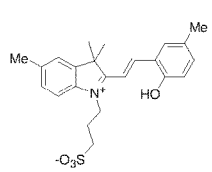
Figure 6X:
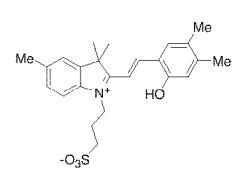

Referring now to FIGS. 6A-6QQ, the structures of 43 photoacids designed based on FIG. 3A including the photoacids 1 and 40 are shown. All of them have been synthesized. These photoacids have TCF and indolinium derivatives (including benzothiazolium) as the EA part, and the phenol and indazole derivatives as the NuH part. Analogs of photoacid 1 have been extensively studied. Electron-donating groups (-Me and —OMe) on the phenolic moiety increase the stability of the photoacid towards hydrolysis and faster the reverse reaction rate. Photoacids with extended conjugated structures can absorb light and thus function at longer wavelengths than photoacid 1. For example, photoacid 20 has a maximum absorption at 538 nm in 95% ethanol solution, which is about 100 nm longer than that of photoacid 1. Photoacids 10, 17 and 39 have acrylate moieties. They can be used to make photoacid polymers via chain-growth polymerization or thiol-ene reaction. Using indazole as NuH lowers the dark acidity of the photoacids, which allows them function in a relatively basic condition. For example, photoacid 34 can reversibly release a proton in a PBS buffer with a pH of 7.4, which is the common physiological pH. In photoacid 34, a benzothiazolium is used as the EA part since it improves the reversibility of the photoreaction. For comparison, photoacid 29 with a common indolinium EA has such a slow reverse reaction rate that it is essentially an irreversible photoacid.

TABLE 1

Type 1 Photoacids

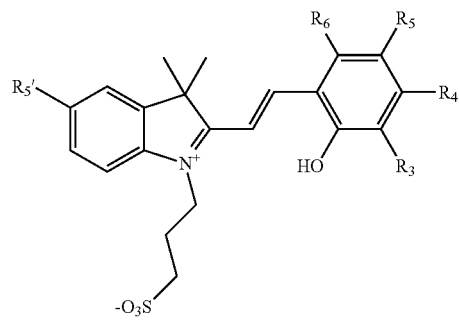

| Photoacid | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| R6 | H | H | H | H | H | H | H | H | H | H | H | H | OMe | H | H |
| R5 | H | Me | NO2 | CO2H | NO2 | H | H | H | OH | OCOCH=CH2 | H | OMe | H | H | Me |
| R4 | H | H | H | H | H | H | H | OH | H | H | H | H | OMe | Me | Me |
| R3 | H | H | H | H | OMe | OMe | OH | H | H | H | Me | H | H | H | H |
| R5' | H | H | H | H | H | H | H | H | H | H | H | H | H | H | H |

| | Photoacid | 16 | 17 | 18 | 19 | 20 | 21 | 22 | 23 | 24 | 25 | 26 |
|---|---|---|---|---|---|---|---|---|---|---|---|---|
| | R6 | H | H | H | H | H | H | H | H | H | H | OMe |
| | R5 | OMe | CH2OCOCH=CH2 | H | H | CH2Cl | H | H | Me | Me | $H_7$ | H |
| | R4 | OMe | H | H | H | H | OMe | Me | H | Me | H | $OMe_5$ |
| | R3 | H | H | H | H | H | H | H | H | H | OMe | H |
| | R5' | H | H | OMe | H | Me | Me | Me | Me | Me | Me | Me |

TABLE 1-continued
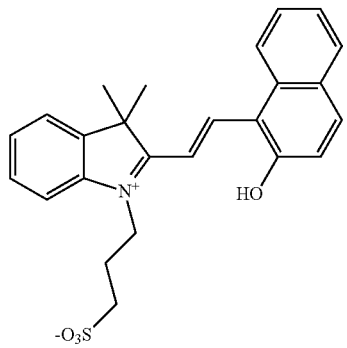
27
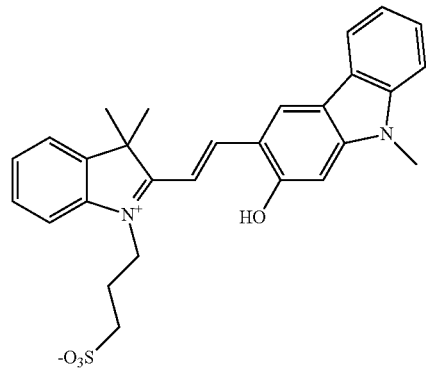
28
| TABLE 2 |
|---|
| Type 2 Photoacids |
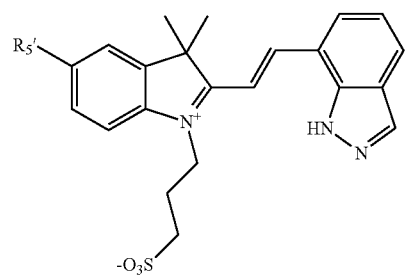
R5'
H 29
Me 30
OMe 31
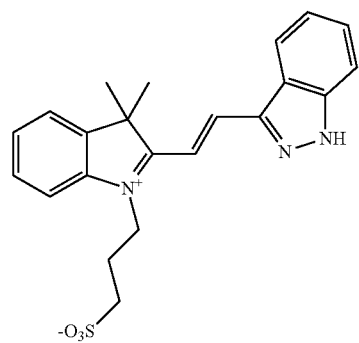
32
| TABLE 2-continued |
|---|
| Type 2 Photoacids |
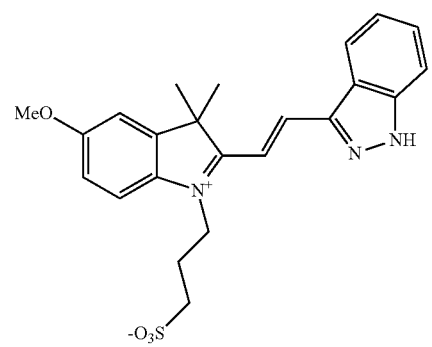
33
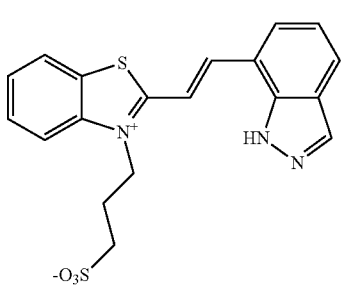
34

TABLE 3

Type 3 Photoacids

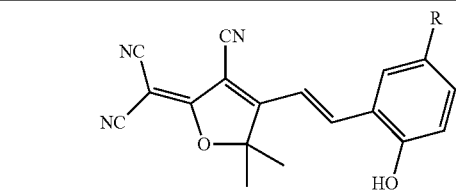

R = H 35
R = CH$_2$Cl 36
R = COOH 37
R = NO$_2$ 38
R = CH$_2$OCOCH=CH$_2$ 39

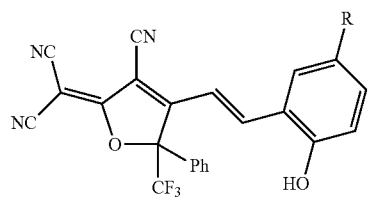

R' = H 40
R = OMe 41

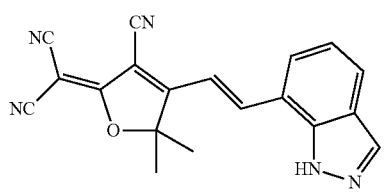 [SMILES: CC1(C)OC(=C(C#N)C#N)C(C#N)=C1/C=C/c1cccc2cn[nH]c12]
42

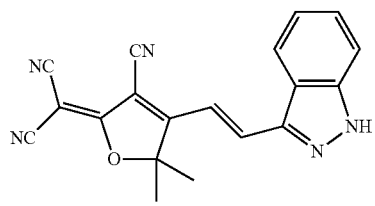 [SMILES: CC1(C)OC(=C(C#N)C#N)C(C#N)=C1/C=C/c1n[nH]c2ccccc12]
43

Example applications for disclosed PAHs include, but are not limited to, photo-induced pH jumping (e.g., for biological studies) photo-switchable electrically conducting materials, hydrogel valve formation, link to protein/DNA as catalyst to alter biological functionality of a molecule, and/or formation of a "releasing" polymer (e.g. upon light exposure), release of fragrance, reagent, or drug. Other example applications include control of pH-sensitive processes, material processing including polymer processing, photo-rechargeable batteries, and other energy conversion applications.

It is noted that different applications require different time scales of the proton-dissociation state. Although the lifetime of the proton dissociation state should be long enough for the proton to effectively transfer from the photoacid to the target molecule, it is not true that a very stable proton dissociation state is always desirable. For some applications, e.g. photoswitchable conducting materials described below, the proton dissociation state must be so stable that photo-irradiation with a different wavelength or intensive heating is required to switch it back to the proton association state. This may be called a bistable photoacid. For other applications, it is desirable that the two states can be switched by simply turning a light on and off. In this case, the lifetime of the proton dissociation state should be short enough for a quick response to the dark state while being long enough for effective proton transfer.

For example, disclosed photoacids can provide a general and practical way to control and drive numerous chemical processes with photo energy. In this application, the potentials of the long-lived photoacids in catalyzing chemical reactions, developing materials with photoresponsive volume and mechanical property change, preparing photo-controlled drug-delivery polymers, designing photo-switchable electronic materials, and converting photoenergy to electronic energy are included. None of these applications can be realized with known photoacids.

As noted above, disclosed photoacids can catalyze a variety of chemical reactions, such as an esterification reaction using photoacid 1. Theoretically, all the chemical reactions that are catalyzed by Bronsted acids may be controlled/driven by light using disclosed PAHs. Besides the esterification reaction, reactions such as hydrolysis of esters and amides, aldol condensation, the Mannichi reaction, electrophilic reactions of electron rich aromatics, the Diels Alder reaction, and cationic polymerization are other examples. Covalently linking disclosed PAHs to polymer resins can provide recyclable heterogeneous photocatalysts that eliminate the requirements of strong acids for many chemical reactions.

Figures 5A, 5B:
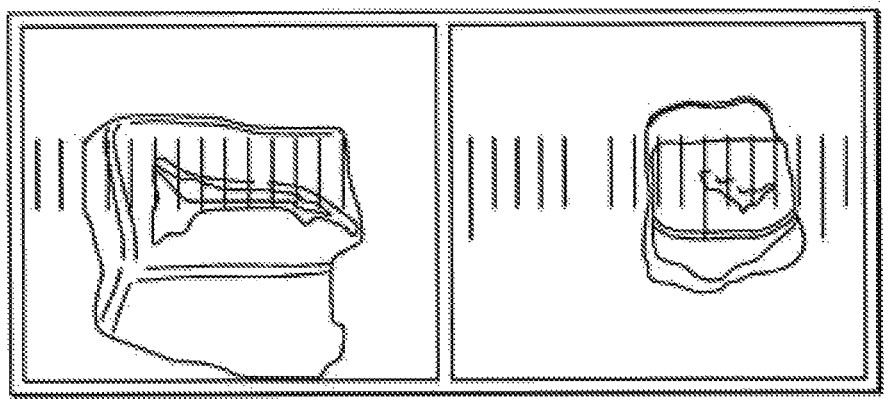
FIGS. 5A and 5B show the dimension of a hydrogel including a disclosed PAH before and after irradiation, respectively, where the volume of the hydrogel after irradiation is shown to have changed to about ⅛ of its initial volume, according to an example embodiment.

Disclosed PAHs can provide photoresponsive volume change and mechanical properties to certain materials, such as polymeric materials. As described below relative to FIGS. 5A and 5B, when a pH sensitive polymer is soaked in a solution of photoacid 1, the volume of the polymer was found to be reduced to about ⅛ of its initial volume upon irradiation. This process was not reversible. However, new pH sensitive hydrogels can reversibly change its volume after being treated with disclosed PAHs. Such hydrogels can be crosslinked copolymers of acrylic acid and acrylamide. The ratio of the two monomers and the crosslinker, e.g. N,N'-methylene bisacrylamide can be varied to find a material that has both large volume change and good reversibility. In addition, covalently linking of disclosed photoacids with pH sensitive polymers can make the polymers themselves photoresponsive actuators and artificial muscles. Disclosed PAHs also provide a new way to design materials with photoresponsive mechanic properties.

Polymers can be synthesized with disclosed PAHs and weak-bases such as imidazole or pyrazole grafted on the main chain via flexible side chains. Upon irradiation, the PAHs will transfer protons to the bases, and thus form ionic bonds. The flexible side chains will allow necessary rearrangement of the cations and anions to maximize the ionic interaction in domains. The mechanical strength of the irradiated polymer will increase due to the photo-generated ionic bonds. In the dark, the protons will transfer back to the more basic photoacidic anion, which eliminate the ionic bonds. Therefore, the mechanical properties of the copolymers can be reversibly controlled by photoirradiation. The mechanical properties can be measured by an ATS Tensile Tester/Extensiometer in the dark and under photo-irradiation.

Biocompatible polymers linked with disclosed PAHs may be used as photoresponsive drug delivery materials. At least two types of polymers can be used. As described above, photoacid 1 can greatly change the volume of a pH sensitive polymer upon irradiation. PH sensitive polymers can be grafted with the disclosed photoacids. Microspheres of this type of polymers loaded with drugs can change their volume upon photoirradiation, and thus release the drugs. A second type of material is polymer conjugated with both the PAHs and the drugs. The linkage between the polymer main chain and the drug can to be hydrolyzed by acid, for example hydrazone bonds. Upon irradiation, the PAHs can cleave the drug molecules from polymer main-chain, which cause drug release.

Disclosed PAHs can provide photo-switchable electrically conducting materials based on protonation and deprotonation of certain materials such as polyaniline. Photo-switchable electrically conductive materials have been of interest since the early stage of organic electronic materials due to its potentials in electronics and data storage. However, after about three decades, the magnitude of the reversible electrical conductivity change induced by photo-irradiation is still very small. For example, a material that can reversibly change its conductivity of ~1 fold at $10^{-1}$ S/cm has been reported. Another publication disclosed a photo-switchable material that showed a 2 order of magnitude electrical conductivity change. However, this material was a semiconductor rather than a conductor, which means it needs both light and gate voltage to control electricity. The emeraldine base form of polyaniline (PANI-EB) is an electrical insulator with a conductivity of ~$10^{-10}$ S/cm. When it is protonized, its electrical conductivity increases up to ~$10^{2}$ S/cm.

Therefore, composites of PANI-EB and a bistable photo acid may be switched from a low electrically conductive state to a highly electrically conductive state by photo-irradiation using disclosed PAHs, and switched back to a low electrically conductive state by irradiation at a different wavelength or intensive heating by, e.g. laser ablation. It has been shown that composites of PANI-EB and a photo-acid generator (PAG) can be converted from a low electrically conductive state to a high electrically conductive state. The record of the photo-induced conductivity without any post treatment ($10^{-1}$ S/cm) was recently reported by the Inventor.

Figures 7A, 7B, 7C, 7D:
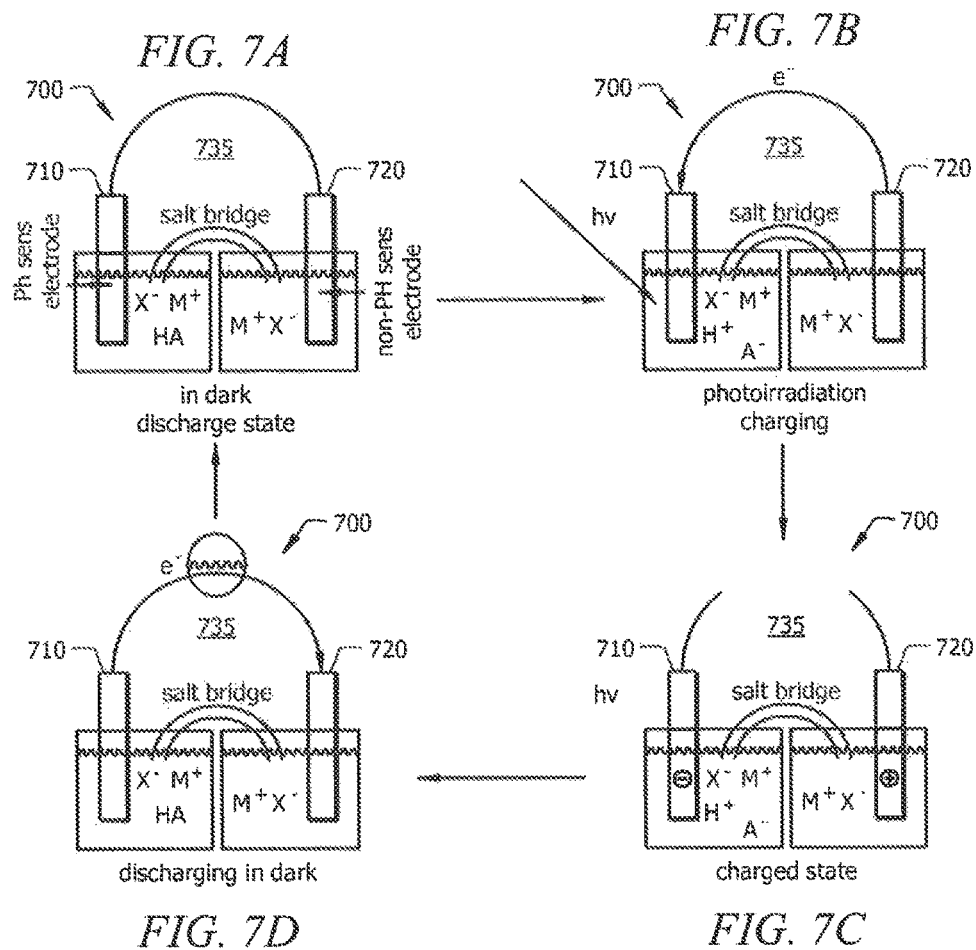
FIGS. 7A-D shows a disclosed photo-chargeable battery comprising a pH sensitive electrode, a non-pH sensitive

Disclosed PAHs can be used for photo-rechargeable batteries. Together with a pH sensitive electrode, disclosed photoacids can be used to convert photoenergy to electrical energy. As depicted in FIGS. 7A-D, a photo-chargeable battery 700 can comprise a pH sensitive electrode 710 (e.g. quinhydrone or antimony electrode), a non-pH sensitive counter electrode 720 such as AgCl, and an electrolyte solution containing disclosed photoacids shown as HA, and a salt bridge 735, shown in various charge states. FIG. 7A shows the photo-chargeable battery 700 in an initial dark discharged state. Upon photoirradiation, the potential of the pH sensitive electrode 710 changes due to the acidity increase of the solution as shown in FIG. 7B, which induces electron transfer between the pH sensitive electrode 710 and the non-pH sensitive electrode 720. The resulting state is a photo-charged high energy state as shown in FIG. 7C. For example, when the electrodes 710 and 720 are quinhydrone and silver gauze electrode, and the electrolyte solution containing the photoacid and the salt KCl, the electrochemical reactions upon irradiation at the two electrodes are:

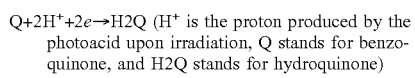
(H⁺ is the proton produced by the photoacid upon irradiation, Q stands for benzoquinone, and H2Q stands for hydroquinone)

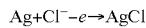

In the dark, the spontaneous proton association of the PAH allows the battery to discharge to the low energy state as shown in FIG. 7D. The electrochemical characterization can be carried out in a three electrode cell using Ag|Ag-Cl|KCl as the reference electrode. In the presence of the reference electrode, both working and counter electrode potentials can be monitored with an electrochemical analyzer.

Disclosed PAHs have a variety other applications, such as for proton transfer which is a common mechanism of many biological processes and many biological materials including DNA and proteins which are pH sensitive. Disclosed PAHs, which allow spatial and temporal control of proton concentration, may become a useful tool for studying biological systems. As noted above, other example applications for disclosed PAHs include photo-induced pH jumping (e.g., for biological studies), photo-switchable electrically conducting materials, hydrogel valve formation, formation of a "releasing" polymer (e.g. upon light exposure), release of fragrance, reagent, or a drug, and energy conversion applications.

EXAMPLES

Disclosed embodiments are further illustrated by the following specific Examples, which should not be construed as limiting the scope or content of this Disclosure in any way.

Experiments were conducted to demonstrate certain applications for disclosed PAHs. As disclosed above, control of chemical reactions with PAHs has been an unattained goal for decades. Therefore, in one experiment, photoacid 1 was used to catalyze a Fisher esterification reaction, which conventionally requires a strong acid catalyst, such as sulfuric acid. A mixture of acetic acid (12.5 mM) which is a weak organic acid and photoacid 1 (3.1 mM) in ethanol was irradiated at 419 and 570 nm. Ethyl acetate was produced and was analyzed by HPLC. The yields were 33%, 50% and 66% for 1, 2, and a 3 hr reaction, respectively. No reaction was detected when the mixture was kept in the dark. This experiment demonstrates that acid-catalyzed reactions can be photo-catalyzed using disclosed PAHs.

In a second experiment, a solution of photoacid 1 was used to alter the volume of a pH sensitive polymer. A hydrogel of crosslinked polyacrylamide was prepared based on a published procedure. It was partially hydrolyzed to a copolymer of polyacrylic acid and polyacrylamide by 1 M NaOH solution. The hydrogel was then cut into cuboids, which were soaked in a mixture of photoacid 1 in water (1 mg/mL). After irradiation, the volume of the hydrogel changed to about ⅛ of its initial volume as shown in the before irradiation scanned image in FIG. 5A and the after irradiation scanned image in FIG. 5B. The hydrogel did not change back to its original volume in dark although the pH of the solution did change back. This is due to the property of the hydrogel, not the PAH, since the hydrogel showed the same behavior when placed in different buffer solutions with different pH values.

While various disclosed embodiments have been described above, it should be understood that they have been presented by way of example only, and not limitation. Numerous changes to the subject matter disclosed herein can be made in accordance with this Disclosure without departing from the spirit or scope of this Disclosure. In addition, while a particular feature may have been disclosed with respect to only one of several implementations, such feature may be combined with one or more other features of the other implementations as may be desired and advantageous for any given or particular application.

Thus, the breadth and scope of the subject matter provided in this Disclosure should not be limited by any of the above explicitly described embodiments. Rather, the scope of this Disclosure should be defined in accordance with the following claims and their equivalents.

The terminology used herein is for the purpose of describing particular embodiments only and is not intended to be limiting. As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which embodiments of the invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The invention claimed is:

1. A photoacid composition, comprising:
   a nucleophilic (NuH) moiety selected from the group consisting of a phenol, a napthol, a pyrazole, an indazole, a triazole and a benzotriazole and having a photodissociable proton;
   an electron accepting (EA) moiety selected from the group consisting of an indolinium, a furan having a trifluoromethyl group, a benzothiophene, an indene and a dicyanoethene; and
   a bridge structure (X) comprising a double-bond selected from the group consisting of a C=N bond and a C=C bond, wherein said bridge structure is bonded to both said NuH moiety and said EA moiety positioned between said NuH moiety and said EA moiety,
   wherein the EA moiety is neutral, and
   wherein said NuH moiety and said EA moiety include respective structure so that said EA moiety bonds to a proton photodissociated form of said NuH moiety during a reversible photoinduced intramolecular ring closing reaction to form a ringed structure and generate a proton H+.

2. The photoacid composition of claim 1, wherein said EA moiety comprises a zwitterion.

3. The photoacid composition of claim 1, wherein said reversible photoinduced intramolecular ring closing reaction results from irradiation.

4. The photoacid composition of claim 1, wherein double-bond comprises a C=N bond.

5. The photoacid composition of claim 1, wherein said double-bond comprises a C=C bond.

6. The photoacid composition of claim 1, wherein said composition comprises a structure selected from the group consisting of a phenol, a napthol, an indazole, a pyrazole, a benzotriazole, a triazole, an indolinium, an indoline, a furan having a trifluoromethyl group, a benzothiophene, an indene and a dicyanomethane.

7. A photoacid of the formula:

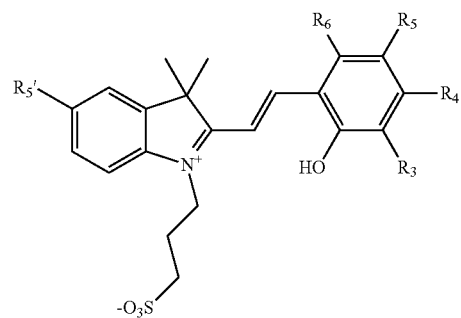

wherein:
$R_3$ is H, OH, Me, or OMe;
$R_4$ is H, OH, Me, or OMe;
$R_5$ is H, OH, $NO_2$, Me, OMe, COOH, OCOCH=$CH_2$, $CH_2$OCOCH=$CH_2$, or $CH_2Cl$;
$R_5'$ is H, Me, or OMe; and
$R_6$ is H or OMe.

8. A photoacid of the formula:

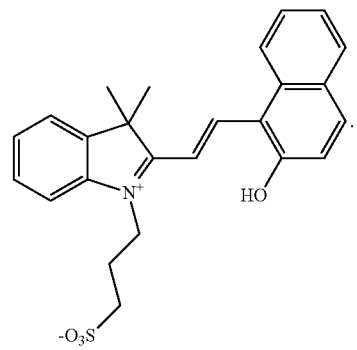

9. A photoacid of the formula:

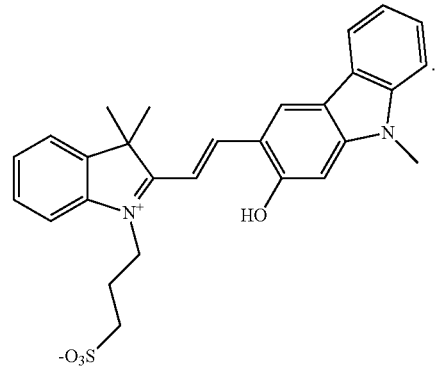

10. A photoacid of the formula:

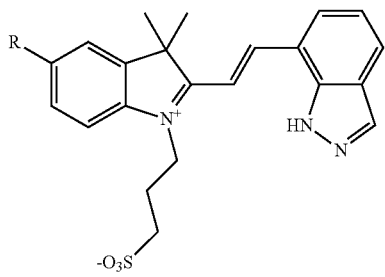

wherein:
R is H, Me, or OMe.

11. The photoacid of claim 10 wherein R is H.

12. A photoacid of the formula:

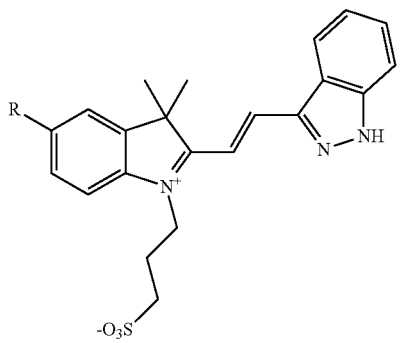

wherein:
R is H or OMe.

13. A photoacid of the formula:

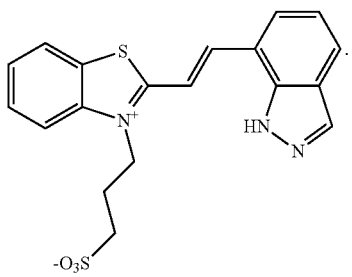

14. A photoacid of the formula:

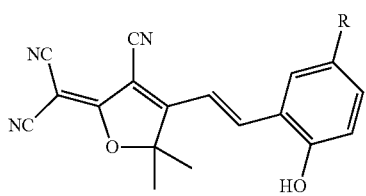

wherein:
R is $NO_2$, COOH, $CH_2OCOCH=CH_2$, or $CH_2Cl$.

15. The photoacid of claim 14 wherein R is $CH_2Cl$.

16. A photoacid of the formula:

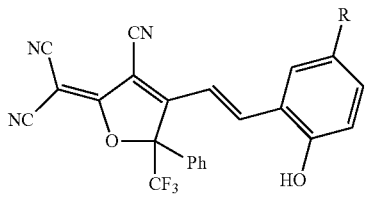

wherein:
R is H or OMe.

17. The photoacid of claim 16 wherein R is H.

18. A photoacid of the formula:

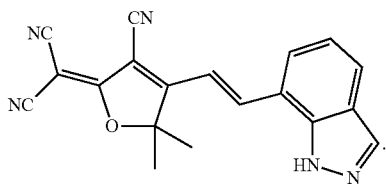 [SMILES: CC1(C)OC(=C(C#N)C#N)C(C#N)=C1/C=C/c1cccc2cn[nH]c12]

19. A photoacid of the formula:

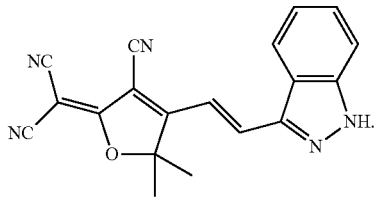 [SMILES: CC1(C)OC(=C(C#N)C#N)C(C#N)=C1/C=C/c1n[nH]c2ccccc12]

20. A photoacid composition, comprising:
a nucleophilic (NuH) moiety selected from the group consisting of a phenol, a napthol, a pyrazole, an indazole, a triazole and a benzotriazole and having a photodissociable proton;
an electron accepting (EA) moiety selected from the group consisting of an indolinium, a furan, a benzothiophene, an indene and a dicyanoethene; and
a bridge structure (X) comprising a C=N bond, wherein said bridge structure is bonded to both said NuH moiety and said EA moiety positioned between said NuH moiety and said EA moiety,
wherein the EA moiety is neutral, and
wherein said NuH moiety and said EA moiety include respective structure so that said EA moiety bonds to a proton photodissociated form of said NuH moiety during a reversible photoinduced intramolecular ring closing reaction to form a ringed structure and generate a proton H+.

* * * * *